United States Patent
Greiner et al.

(10) Patent No.: US 7,453,988 B2
(45) Date of Patent: Nov. 18, 2008

(54) MULTIFUNCTIONAL X-RAY SYSTEM AND METHOD FOR OPERATING IT

(75) Inventors: Hans-Joachim Greiner, Uttenreuth (DE); Mathias Hörnig, Erlangen (DE); Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 45 days.

(21) Appl. No.: 11/473,226

(22) Filed: Jun. 23, 2006

(65) Prior Publication Data

US 2006/0291625 A1    Dec. 28, 2006

(30) Foreign Application Priority Data

Jun. 24, 2005   (DE) .................. 10 2005 029 462

(51) Int. Cl.
*H05G 1/54* (2006.01)
*H05G 1/58* (2006.01)
(52) U.S. Cl. .................. 378/116; 378/117; 378/150
(58) Field of Classification Search .......... 378/116, 378/117, 150
See application file for complete search history.

(56) References Cited

U.S. PATENT DOCUMENTS

| 3,947,689 A | * | 3/1976 | Wagner | 378/151 |
| 4,137,460 A | * | 1/1979 | Fitzsimmons et al. | 378/151 |
| 4,152,604 A | * | 5/1979 | Burbury | 378/98 |

FOREIGN PATENT DOCUMENTS

| DE | 1 827 904 U | 3/1961 |
| DE | 2 141 676 A | 2/1973 |

OTHER PUBLICATIONS

Regelung EN/IEC 60601-1-3 2006Q14455.
German Office Action dated Sep. 14, 2007.

* cited by examiner

*Primary Examiner*—Edward J Glick
*Assistant Examiner*—Thomas R Artman
(74) *Attorney, Agent, or Firm*—Harness, Dickey & Pierce, P.L.C.

(57) ABSTRACT

To comply with radiation protection provisions that differ from one another for different operating functions without operational restrictions, a radiation protection system is provided in the case of a multifunctional x-ray system for a solid state detector assigned to the x-ray system. The radiation protection system includes a device for restricting the current outer contours of an x-radiation field to bounding outer contours dependent on the selected operating function of the x-ray system.

21 Claims, 4 Drawing Sheets

US 7,453,988 B2

MULTIFUNCTIONAL X-RAY SYSTEM AND METHOD FOR OPERATING IT

PRIORITY STATEMENT

The present application hereby claims priority under 35 U.S.C. §119 on German patent application number DE 10 2005 029 462.6 filed Jun. 24, 2005, the entire contents of which is hereby incorporated herein by reference.

BACKGROUND

X-ray systems are generally subdivided with regard to radiation protection conditions in accordance with their operating function such as, for example, fluoroscopy or radiography. Depending on operating function, it is necessary to have appropriate radiation protection for national or international approval of the x-ray system, in order to ensure patient protection and product reliability. For example, in addition to a shield at the underside of the solid state detector averted from the x-radiation, in Germany a solid state detector that is assigned to a fluoroscopic x-ray system must, in accordance with regulation EN/IEC 60601-1-3, additionally have a lateral shield and, at the top side facing the x-radiation, a shield on the side of the top edge which has a width of at least 30 mm.

If an x-ray system is multifunctional, that is to say equipped with a number of operating functions, a solid state detector approved for all operating functions must fulfill the radiation protection provisions in accordance with the operating function having the most stringent regulations. This leads in the case of multifunctional x-ray systems to restrictions on the remaining operating functions.

If a solid state detector is assigned to a radiographic x-ray system that has an additional fluoroscopic function, for example the so-called "positioning", it must then fulfill the regulations for a fluoroscopic x-ray system, that is to say it must have at the top side a shield on the side of the top edge which has a width of at least 30 mm. If the aim is to take an image of the lung with the aid of the radiographic function, it would, however, be important to keep the distance between the side edge and active surface as small as possible and, specifically, much below 30 mm in order to also image the lung tips completely.

SUMMARY

An object of at least one embodiment of the present invention is to reduce operational restrictions in the case of a multifunctional x-ray system while complying with all radiation protection provisions.

An object may be achieved, according to at least one embodiment of the invention, by way of a multifunctional x-ray system, and/or by a method for operating a multifunctional x-ray system.

The inventive multifunctional x-ray system of at least one embodiment includes a radiation protection system for a solid state detector assigned to the x-ray system permits the device(s) for restricting the current outer contours of the x-radiation field, and the dependence of the bounding outer contours on the selected operating function of the x-ray system to be used without imposing a restriction on one of the operating functions to comply with radiation protection provisions that differ from one another for different operating functions; for example, given a medical x-ray system having a radiographic function and a fluoroscopic function, it is possible to comply in the case of the latter with the radiation protection provision EN/IEC 60601-1-3, chapter 29.207, without restricting the radiographic function. To this end, according to one refinement of at least one embodiment of the invention the bounding outer contours have a greater spacing from the outer lateral edge of the solid state detector in the case of the fluoroscopic function than in the case of the radiographic function.

The x-ray system equipped according to at least one embodiment of the invention with a system-side radiation protection system for the solid state detector saves at the solid state detector at least a portion of a complicated lead shield that is bulky and heavy.

According to a further refinement of at least one embodiment of the invention, in the case of an x-ray system having a beam diaphragm it is provided to co-use the beam diaphragm as means for restricting the current outer contours of the x-radiation field by way of the radiation protection system; this use of a component already present simultaneously saves costs, and likewise the outlay on installing an additional component and connecting it to the x-ray system.

In order to enable simple operation of the x-ray system, the radiation protection system advantageously has a control and regulation unit for restricting the current outer contours of the x-radiation field.

BRIEF DESCRIPTION OF THE DRAWINGS

Embodiments of the invention and further advantageous refinements are explained in more detail below, including the drawings with the aid of schematics of example embodiments, without thereby restricting the invention to these example embodiments. In the drawings.

DETAILED DESCRIPTION OF THE EXAMPLE EMBODIMENTS

Figure 1:
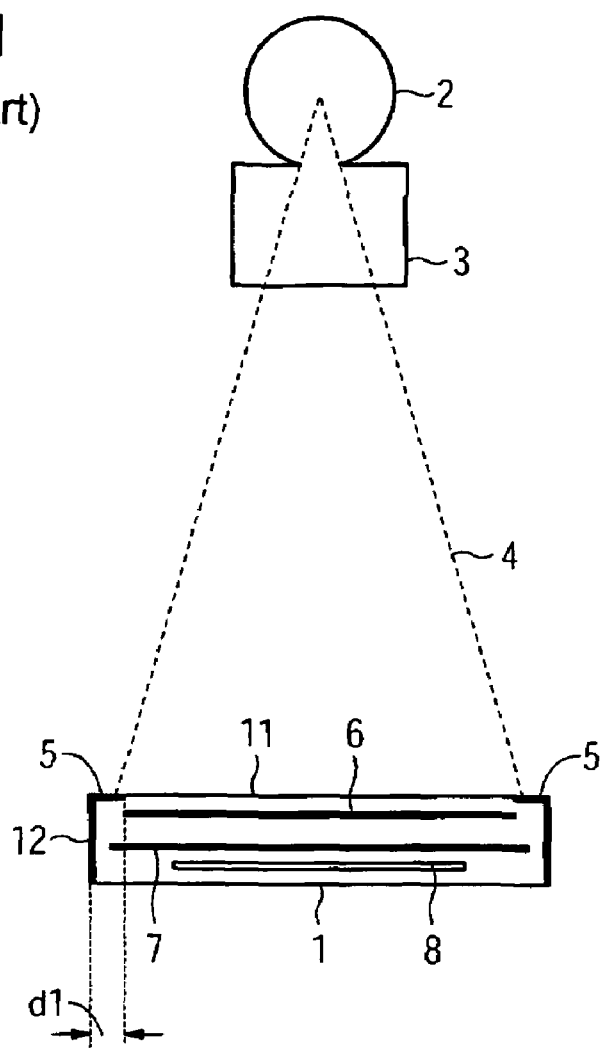
FIG. 1 is a schematic of a section of an x-ray system having an assigned solid state detector according to the prior art.
Figure 2:
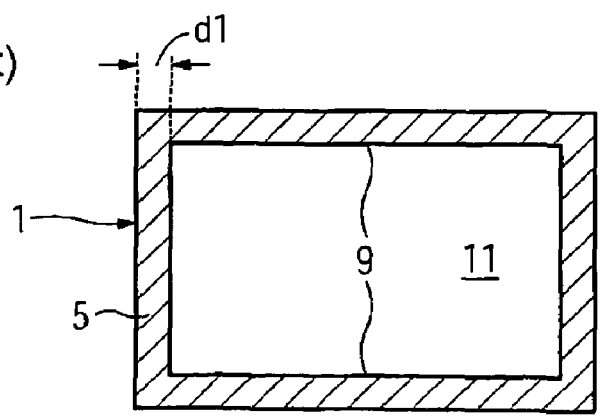
FIG. 2 shows a plan view of bounding outer contours on the solid state detector in accordance with FIG. 1, using the fluoroscopic function and radiographic function.

As a section from an x-ray system according to the prior art that is equipped with a fluoroscopic function and a radiographic function, FIG. 1 shows an x-ray source 2 having a collimator 3 and an assigned solid state detector 1. The solid state detector 1 includes x ray shields 5; 7; 12 in addition to an active surface 6 for converting an x-radiation 4 into image data, and an electronics unit 8. In order, for example, to fulfill the radiation protection provisions EN/IEC 60601-1-3 for the fluoroscopic function, the solid state detector 1 has a lower shield 7, a shield 5, on the side of the top edge, of width d1, and a lateral shield 12. The x-ray source 2 generates the x radiation 4 that impinges on the top side of the solid state detector 1. As shown in FIG. 2, the result of this is to define a maximum x-radiation field 11 that is formed from the effective impingement surface of the x radiation minus the area shielded by the shield 5, on the side of the top edge, of width d1. The maximum x-radiation field 11 is restricted by its bounding outer contours 9.

In the case of the x-ray system according to the prior art, there is the problem that complying with radiation protection provisions when using the fluoroscopic function requires the presence of the above-described shield 5; 7; 12, in order to bound the x-radiation field 11. Consequently, the same shield is present and the same maximum x-radiation field 11 is defined in the case of the radiographic function, as well, although a reduced shielding would be desirable here.

Figure 3:
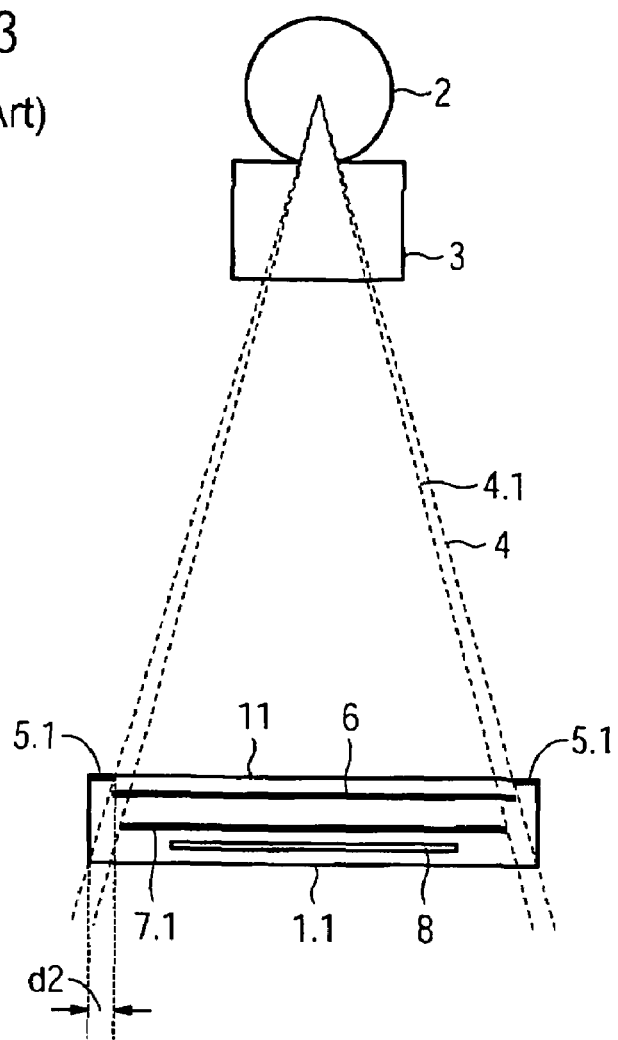
FIG. 3 is a schematic of a section of an x-ray system having an assigned solid state detector with reduced shielding, using a fluoroscopic function according to the prior art.
Figure 4:
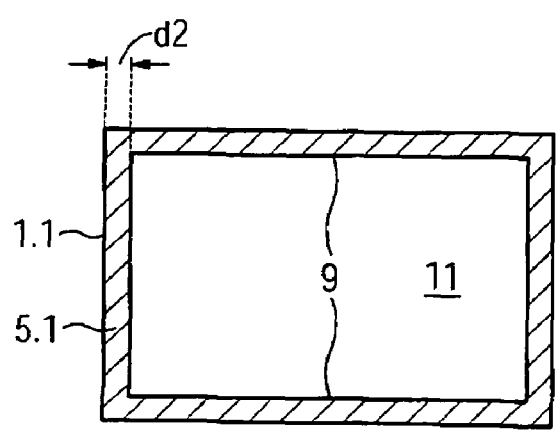
FIG. 4 shows a plan view of bounding outer contours on the solid state detector in accordance with FIG. 3, using the fluoroscopic function.

It is shown in FIGS. 3 and 4 what are the effects of a reduced lateral shield 5.1 and a reduced lower shield 7.1 of a solid state detector 1.1 with reduced shielding during use of the fluoroscopic function in an x-ray system according to the prior art: the radiation protection is inadequate and radiation escapes laterally through a marginal ray 4.1 of the x-radiation 4. The second possibility of maintaining the radiation protection in the case of an x-ray system according to the prior art is, in addition to accepting restrictions for at least one operating function, a complicated interchange of the solid state detectors 1; 1.1, depending on the operating function currently in use.

In at least one embodiment of the invention, a problem described may be reduced or even solved by providing the x-ray system according to at least one embodiment of the invention with a system-side radiation protection system for a solid state detector 1.1 having reduced shielding, which radiation protection system co-uses, for example—as shown in FIG. 5 to FIG. 8—a beam diaphragm 10 as means for restricting the current x-radiation field.

Figure 5:
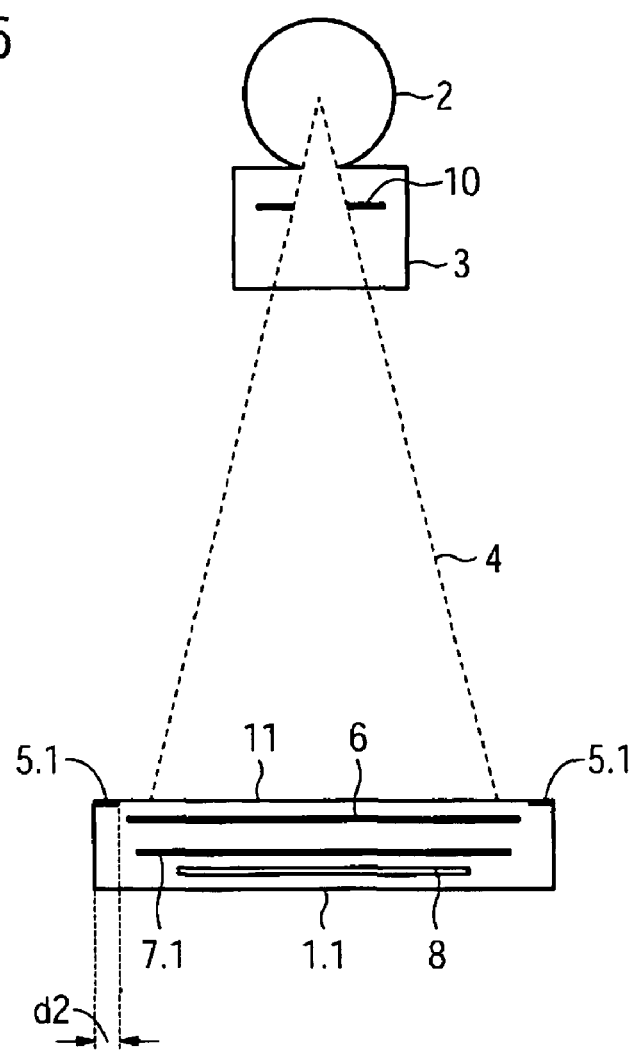
FIG. 5 is a schematic of a section of an inventive x-ray system having an assigned solid state detector with reduced shielding, using the fluoroscopic function.
Figure 7:
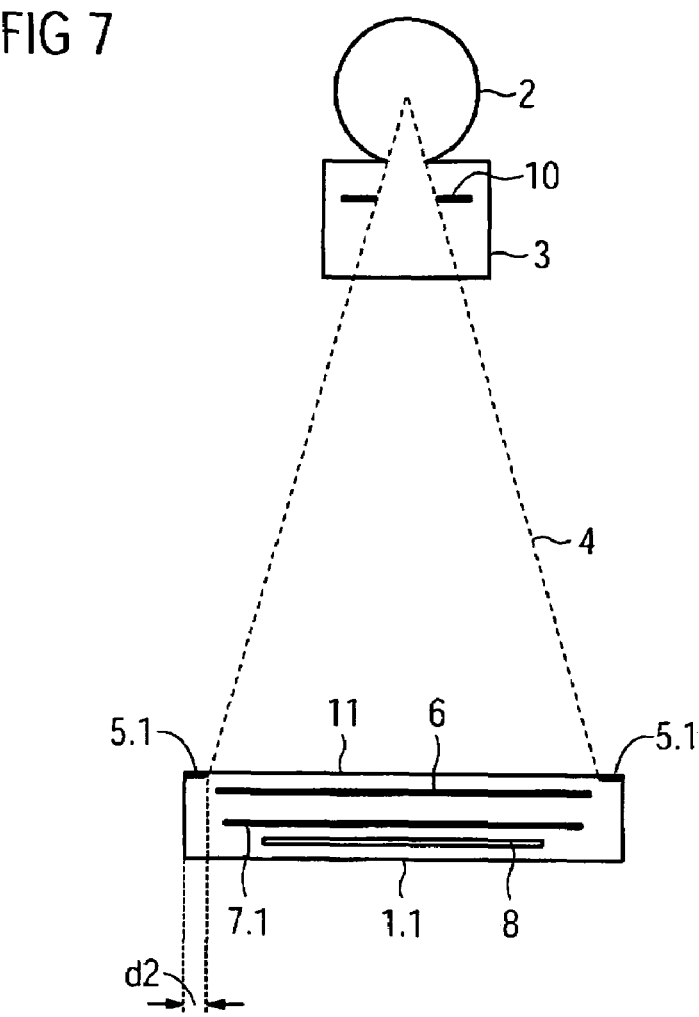
FIG. 7 is a schematic of a section of an inventive x-ray system having an assigned solid state detector with reduced shielding, using the radiographic function.

FIG. 5 shows a section from an inventive x-ray system using the fluoroscopic function, having an assigned solid state detector 1.1 with reduced shielding, and FIG. 7 shows the same section using the radiographic function.

Figure 6:
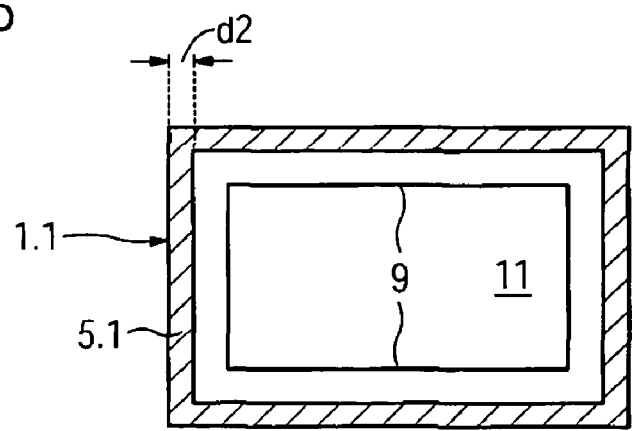
FIG. 6 shows a plan view of bounding outer contours on the solid state detector in accordance with FIG. 5, using the fluoroscopic function.
Figure 8:
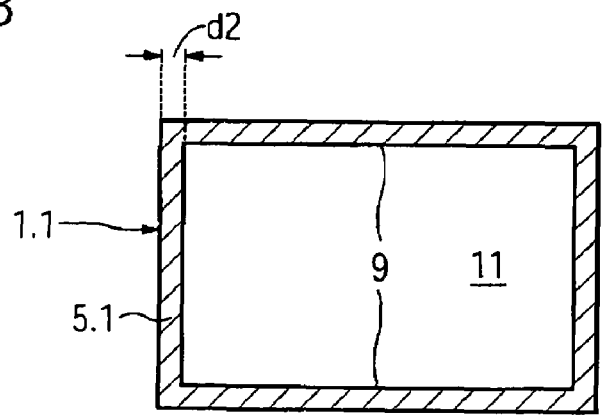
FIG. 8 is a plan view of bounding outer contours on the solid state detector in accordance with FIG. 7, using the radiographic function.

It is to be seen by comparison—specifically also in FIG. 6 and FIG. 8—that when use is made of the solid state detector 1.1 with a reduced shield 5.1; 7.1, at least one embodiment of the invention can implement different bounding outer contours 9, and thus maximum x-radiation fields 11 of different size. There is no longer any need in the case of the inventive x-ray system for a troublesome and complicated exchange of the solid state detector 1 for a solid state detector 1.1 with a reduced shield 5.1; 7.1, and vice versa.

The reduced shielding includes a second lower shield 7.1 and a second shield 5.1, on the side of the top edge, of a second width d2 that is much smaller than the first width d1 of the shield 5 on the side of the top edge, which is necessary in the prior art in order to comply with radiation protection provisions for fluoroscopy. The radiation protection is still performed only partially by the reduced shield 5.1, 7.1, but chiefly by the inventive radiation protection system.

The radiation protection system advantageously includes a control and regulation unit for setting the bounding outer contours 9 for the x-radiation field 11. This control and regulation unit monitors the compliance with the bounding outer contours 9 as a function of the current operating function of the x-ray system. In the case of the fluoroscopic function, the bounding outer contours advantageously have a prescribed minimum distance from the outer lateral edge of the solid state detector, in particular 30 mm. The radiation protection provisions of regulation EN/IEC 60601-1-3 are thereby complied with.

According to one design of at least one embodiment of the invention, it is provided for the control and regulation unit to block the x-ray source with reference to the emission of x-radiation when the current outer contours of the x-radiation field exceed the bounding outer contours. This can be provided in such a way that the control of the x-ray system passes on the set parameters to the control and regulation unit of the radiation protection system before application of the x-radiation. A calculating unit integrated, for example, in the control and regulation unit of the radiation protection system calculates the position of the current outer contours of the x-radiation field. If these exceed the bounding outer contours of the respective operating function, the control and regulation unit of the radiation protection system blocks the application of x-radiation until the current outer contours no longer exceed the bounding outer contours.

The bounding outer contours for the respective operating functions are defined, for example, before the multifunctional x-ray system is commissioned, in accordance with the radiation protection provisions valid up to this point in time, and are permanently set in the x-ray system.

According to one design of at least one embodiment of the invention, it is provided for the current outer contours of the x-radiation field to be automatically checked with reference to the bounding outer contours by way of the control and regulation unit in the event of variations in the respective focus-detector distance and/or in the irradiation angle of the x-radiation. Thus, for example, if the focus-detector distance (SID: Source Image Distance) is changed during the operation of the x-ray system, if the irradiation angle of the x-radiation is varied, or if another system-relevant change takes place, the current outer contours are then checked and subsequently readjusted so as to prevent the bounding outer contours from being exceeded. This is carried out automatically by the control and regulation unit of the radiation protection system. For example, current outer contours can be simulated in an arithmetic logic unit, compared with the bounding outer contours and appropriately regulated.

The bounding outer contours of the x-radiation field are expediently coupled to the image format of the solid state detector. This ensures that radiation protection provisions are complied with even when use is made of solid state detectors with image formats of different size. This can be implemented by having the x-ray system adapt the bounding outer contours automatically as soon as it receives information relating to the image format. The information can be made accessible to the x-ray system via a sensor, via a user or via the image system.

At least one embodiment of the invention may be summarized briefly as follows: In order to ensure compliance with radiation protection provisions that differ from one another for different operating functions without operational restrictions, a radiation protection system is provided in the case of a multifunctional x-ray system for a solid state detector 1.1 assigned to the x-ray system, the radiation protection system having a device for restricting the current outer contours of an x-radiation field to bounding outer contours 9 dependent on the selected operating function of the x-ray system.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A multifunctional x-ray system, comprising:
a radiation protection system for a solid state detector assigned to the x-ray system, the radiation protection system including a device to restrict current outer contours of an x-radiation field to bounding outer contours dependent on a selected operating function of the x-ray system; wherein
operating functions of the x-ray system are different imaging functions,
the x-ray system has a radiographic function as a first operating function and a fluoroscopic function as a second operating function, and
the bounding outer contours include a greater spacing from the outer lateral edge of the solid state detector in the case of the fluoroscopic function than in the case of the radiographic function.

2. The x-ray system as claimed in claim 1, wherein the radiation protection system co-uses a beam diaphragm as the device to restrict the current outer contours of the x-radiation field.

3. The x-ray system as claimed in claim 1, wherein the bounding outer contours include a prescribed minimum distance from the outer lateral edge of the solid state detector in the case of the fluoroscopic function.

4. The x-ray system as claimed in claim 3, wherein the minimum distance is 30 mm.

5. The x-ray system as claimed in claim 1, wherein the radiation protection system has a control and regulation unit for restricting the current outer contours of the x-radiation field.

6. The x-ray system as claimed in claim 5, further comprising:
an x-ray source for emitting x-radiation; wherein
the x-ray source is blocked by use of the control and regulation unit with reference to the emission of x-radiation when the current outer contours of the x-radiation field exceed the bounding outer contours.

7. The x-ray system as claimed in claim 5, wherein the current outer contours of the x-radiation field are automatically superimposed with reference to the bounding outer contours via the control and regulation unit in the event of variations in the respective focus-detector distance.

8. The x-ray system as claimed in claim 5, wherein the current outer contours of the x-radiation field are automatically checked with reference to the bounding outer contours via the control and regulation unit in the event of variations in the respective irradiation angle of the x-radiation.

9. The x-ray system as claimed in claim 5, wherein the control unit includes a drive for the beam diaphragms.

10. The x-ray system as claimed in claim 5, further comprising:
an x-ray source for emitting x-radiation; wherein
the x-ray source is blocked by use of the control and regulation unit with reference to the emission of x-radiation when the current outer contours of the x-radiation field exceed the bounding outer contours.

11. The x-ray system as claimed in claim 1, wherein the bounding outer contours of the x-radiation field are coupled to the image format of the solid state detector.

12. The x-ray system as claimed in claim 1, wherein the bounding outer contours of the x-radiation field are fixed for the respective operating function of the x-ray system in such a way that corresponding radiation protection provisions are fulfillable.

13. The x-ray system as claimed in claim 12, wherein radiation protection provisions according to standard EN/IEC 60601-2-3 are fulfillable in the case of the fluoroscopic function.

14. The x-ray system as claimed in claim 1, wherein the x-ray system is formed by a medical radiographic x-ray system having an additional fluoroscopic function.

15. The x-ray system as claimed in claim 14, wherein the additional fluoroscopic function is a positioning function.

16. The x-ray system as claimed in claim 14, wherein radiation protection provisions according to standard EN/IEC 60601-2-3 are fulfillable in the case of the fluoroscopic function.

17. A method for operating a multifunctional x-ray system including a radiation protection system for a solid state detector assigned to the x-ray system, the method comprising:
restricting, via the radiation protection system, current outer contours of an x-radiation field to bounding outer contours as a function of the selected operating function; wherein
operating functions of the x-ray system are different imaging functions,
the x-ray system has a radiographic function as a first operating function and a fluoroscopic function as a second operating function, and
the bounding outer contours include a greater spacing from the outer lateral edge of the solid state detector in the case of the fluoroscopic function than in the case of the radiographic function.

18. The method as claimed in claim 17, for operating a multifunctional x-ray system in which information relating to variations in respective acquisition parameters is passed on to a control and regulation unit of the radiation protection system, evaluated by the latter and used to restrict the current outer contours to the respective bounding outer contours.

19. A computer readable medium storing executable instructions thereon, which when executed by a computer cause the computer to carry out the method as claimed in claim 17.

20. A computer readable medium including program segments for, when executed on a computer, causing the computer to implement the method of claim 17.

21. A multifunctional x-ray system, comprising:
a radiation protection system for a solid state detector assigned to the x-ray system, the radiation protection system including means for restricting current outer contours of an x-radiation field to bounding outer contours dependent on a selected operating function of the x-ray system; wherein
operating functions of the x-ray system are different imaging functions,
the x-ray system has a radiographic function as a first operating function and a fluoroscopic function as a second operating function, and
the bounding outer contours include a greater spacing from the outer lateral edge of the solid state detector in the case of the fluoroscopic function than in the case of the radiographic function.

* * * * *